United States Patent
Forestiere et al.

(10) Patent No.: US 7,411,105 B2
(45) Date of Patent: Aug. 12, 2008

(54) PROCESS AND INSTALLATION FOR THE OLIGOMERIZATION OF OLEFINS THAT USE A MEMBRANE SEPARATION

(75) Inventors: Alain Forestiere, Vernaison (FR); Frederic Favre, Saint Fons (FR); Arnaud Baudot, Lyons (FR); Laurent Bournay, Chaussan (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/639,307

(22) Filed: Dec. 15, 2006

(65) Prior Publication Data
US 2007/0088186 A1    Apr. 19, 2007

Related U.S. Application Data

(63) Continuation of application No. PCT/FR2006/000535, filed on Mar. 10, 2006.

(30) Foreign Application Priority Data
Apr. 11, 2005   (FR)   ................. 05 03600

(51) Int. Cl.
*C07C 2/02*  (2006.01)
*C07C 7/00*  (2006.01)
*C07C 7/144*  (2006.01)

(52) U.S. Cl. ........... 585/531; 585/324; 585/502; 585/510; 585/520; 585/809; 585/818

(58) Field of Classification Search ................. 585/324, 585/502, 510, 520, 531, 809, 818
See application file for complete search history.

*Primary Examiner*—Glenn Caldarola
*Assistant Examiner*—In Suk Bullock
(74) *Attorney, Agent, or Firm*—Millen, White, Zelano, Branigan, P.C.

(57) ABSTRACT

This invention relates to a process for the oligomerization of olefins that have 2 to 6 carbon atoms comprising at least:
  a) One reaction stage in which a first effluent that comprises oligomers, paraffins and olefins that have not reacted is recovered,
  b) A separation stage that makes it possible to separate a portion of the oligomers that are contained in the effluent from a mixture that comprises oligomers, paraffins and the olefins that have not reacted,
  c) A recycling of a portion of said mixture in the reaction stage, and
  d) A stage for membrane separation of another portion of said mixture so as to draw off a permeate that comprises at least 70% by weight of olefins and a retentate that comprises paraffins and oligomers,
  e) A stage for recovery of oligomers on the retentate.

14 Claims, 1 Drawing Sheet

PROCESS AND INSTALLATION FOR THE OLIGOMERIZATION OF OLEFINS THAT USE A MEMBRANE SEPARATION

This application is a continuation of International Application PCT/FR06/00535 filed Mar. 10, 2006, which claims benefit of priority from French Application 05/03.600 filed Apr. 11, 2005.

FIELD OF THE INVENTION

The invention relates to the field of the oligomerization processes that are designed to produce in particular so-called long oligonieric olefins, i.e., most often having between 4 and 10 carbon atoms, starting from shorter monomeric olefins, i.e., generally having between 2 and 6 carbon atoms.

The oligomerization of olefins is a process that is commonly used in petrochemistry. The monomeric olefins are hydrocarbons of the chemical formula $C_nH_{2n}$. The hydrocarbons that are obtained by this process are also olefins whose chemical formula is $C_mH_{2m}$, with m greater than n. The hydrocarbons that are obtained by this process can also be cross oligomers, whereby the latter are generally obtained by oligomerization of a mixture of short monomeric olefins that often have 2 to 6 carbon atoms, and most often 2 to 4 carbon atoms.

PRIOR ART

The oligomerization reactions are generally used with a supply of (a) high-purity monomeric olefin(s). The most commonly used olefins can be ethylene, propylene, butene and optionally mixtures of these olefins.

In the oligomerization processes, the unconverted olefins are generally separated from the oligomers that are produced before being recycled upstream from the oligomerization reactor. During these recycling operations, the inert impurities that are present in the monomeric olefin, often short paraffins of 2 to 4 carbon atoms, have a tendency to accumulate.

Moreover, the small amounts of hydrogen that are typically introduced into the reactor so as, in particular, to improve the selectivity of the oligomerization process have a tendency to induce hydrogenation of the monomeric olefin into paraffin. The paraffins can also result from the transfer of hydrogen or simply from the degradation of certain portions of the catalyst. In the case where the olefin is ethylene, the associated paraffin is ethane. The paraffins are typically inert with regard to the oligomerization reaction and, just like the impurities mentioned above, they have a tendency to accumulate during the recycling operations.

This accumulation of inert compounds, in this case the impurities and the paraffins, leads to a modification of the composition of the reaction medium at equilibrium, to a reduced level of the concentration of reagents, and to a degradation of the output of the oligomerization process.

It is known and practical to purge a more or less significant portion of the recycled monomeric olefin so as to reduce the concentration of the impurities and to eliminate paraffins. This purging operation leads to a loss in monomeric olefins, even in oligomers of high added value.

It would be advantageous to carry out a separation by distillation of the monomeric olefin and of the associated paraffin that are present in the purging. This separation operation, however, is quite difficult to accomplish. Because of their very close physico-chemical properties, separation of the monomeric olefin from the associated paraffin by separative distillation would require a column that comprises a large number of plates.

The U.S. Pat. No. 4,623,704 describes the use of a membrane separation in a process for polymerization of the ethylene, in which ethylene is recycled by membrane separation of the high-ethylene gaseous effluent that is obtained from the polymerization reactor. This technique, which turns out to be fairly inflexible and inefficient, is difficult to transfer to the oligomerization process.

The U.S. Pat. No. 5,681,908 and U.S. Pat. No. 5,521,264 describe processes for gaseous phase polymerization using means for recycling monomers by techniques for separation by extraction using a solvent. These techniques are relatively complex to implement and are inefficient.

It is also known to use membranes for separating the olefins from the paraffins that are present in the gaseous purges.

The U.S. Pat. No. 6,271,319 describes a process for production of polypropylene comprising the implementation of a polymerization reaction, in a reaction zone, so as to recover an effluent that comprises propylene, propane and polypropylene, whereby said effluent is sent into a separation stage that makes it possible to separate the polypropylene from a gas stream, whereby said gas stream is then passed into a membrane that is selective for propylene for recovering a propylene-rich stream and a propane-rich stream, whereby the propylene-rich stream is then recycled in the reaction zone.

The U.S. Pat. No. 6,414,202 and U.S. Pat. No. 6,525,236 describe processes for producing, from propylene, respectively isopropanol and cumene. These processes also implement a reaction in a reaction zone so as to recover an effluent that comprises propylene, propane and the product in question, whereby said effluent is then sent into a stage for separation that makes it possible to separate the alcohol or the cumene from a gas stream, whereby said gas stream is then passed into a membrane that is selective for propylene to recover a propylene-rich stream and a propane-rich stream, whereby the propylene-rich stream is then recycled in the reaction zone.

The processes that are described above are not oligomerization processes. Moreover, the processes that are described above use modules for membrane separation that are supplied essentially by a mixture of olefins, light paraffins and optionally gas, for example propane, propylene and gases such as oxygen and nitrogen. In no case is the product of the reaction, namely the polypropylene, isopropanol or cumene, as appropriate, present in the membrane separation module.

There is a need for upgrading the purging mixtures in the oligomerization processes by effectively recovering the olefins and the oligomers by membrane separation.

More specifically, there is a need for a process for oligomerization of olefins implementing, on the one hand, a purging so as to limit the accumulation of paraffins, a separation of the olefins in said purging, and, on the other hand, an effective recovery of the oligomers.

SUMMARY OF THE INVENTION

An object of this invention is therefore to provide a process for oligomerization of olefins implementing, on the one hand, a purging so as to limit the accumulation of paraffins, and, on the other hand, a membrane separation in said purging.

Another object of the invention is to upgrade a purging mixture that comprises not only the paraffins and the olefins that have not reacted, but also at least a portion of the oligomers formed during the oligomerization reaction.

Another object of the invention is to improve the overall output of the oligomerization process, as much on the level of the olefin consumption as on the level of the oligomer productivity.

Moreover, another important object of the invention is to facilitate the recovery of the oligomers that are present initially in the purging mixture and to make possible a more intense recovery of these oligomers.

The invention therefore relates to a process for the oligomerization of olefins comprising at least one reaction stage, a separation stage that makes it possible to separate a portion (and typically only one portion) of oligomers that are contained in the effluent that is obtained from the reaction stage, a recycling of a portion of a mixture comprising the non-separated oligomers, paraffins and olefins that have not reacted in the reaction stage, and a stage for membrane separation in the additional portion of said mixture so as to draw off a permeate that comprises at least 70% by weight of olefins, typically recycled, and a retentate that comprises paraffins and oligomers.

In a preferred embodiment that corresponds more specifically to the above-mentioned objects, the retentate is sent into a separation stage that makes it possible to separate the oligomers from the paraffins. The separation that makes it possible to separate the oligomers from the paraffins advantageously can be carried out by condensation of the oligomers. An important aspect of this secondary separation of oligomers is that it is facilitated by the preceding stage of membrane separation: actually, because of the evacuation of the olefins in the permeate, the concentration of the residual oligomers is significantly increased in the retentate. The recovery of these residual oligomers is therefore greatly facilitated and does not require, for example, the use of very low temperatures for their condensation. In parallel, for a given condensation temperature, it is possible to carry out a more intense recovery of these oligomers.

In a preferred embodiment, the permeate is recycled in the reaction stage.

The invention also relates to an installation that makes possible the implementation of the process that is described above.

The description and the figures that are presented below make it possible to more clearly illustrate the embodiments of the process of the invention and will indicate all of the advantages associated with the implementation of this process.

DETAILED DESCRIPTION OF THE INVENTION

Figure 1:
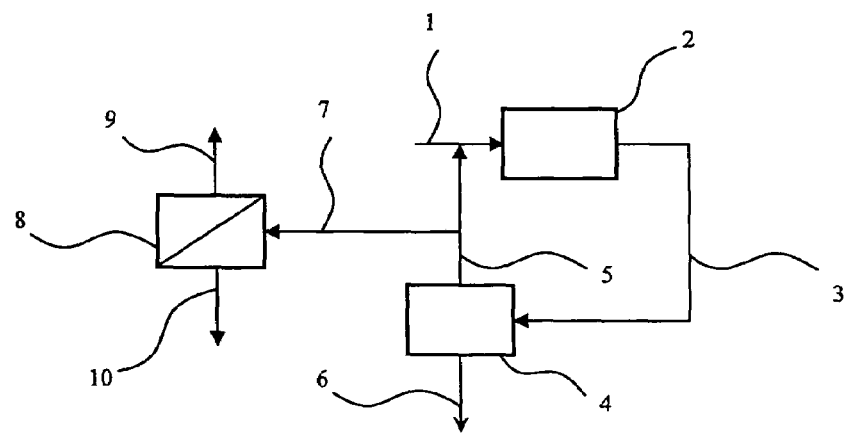
FIG. 1 illustrates, in a nonlimiting manner, the principal stages of the process of the invention.

The invention therefore relates to a process for the oligomerization of olefins that have 2 to 4 carbon atoms comprising at least:
  a) One reaction stage in which a first effluent that comprises oligomers, paraffins and olefins that have not reacted is recovered,
  b) At least one separation stage that makes it possible to separate a portion of the oligomers that are contained in the effluent from a mixture that comprises oligomers, paraffins and the olefins that have not reacted,
  c) A recycling of a portion of said mixture in the reaction stage, and
  d) A stage for membrane separation of another portion of said mixture so as to draw off a permeate that comprises at least 70% by weight of olefins and a retentate that comprises paraffins and oligomers.

The feedstock on which the process of the invention is implemented generally comprises one or more olefin(s), or, more specifically, one or more monomeric olefin(s). Monomeric olefins are defined as olefins that have at least one nonsaturation, i.e., a double bond between two carbon atoms on which it is possible to use the oligomerization reaction.

The expression "oligomerization reaction" generally designates a reaction for coupling N monomeric olefins. This coupling reaction leads to the formation of oligomeric olefins, products of the reaction, each comprising N monomeric olefins.

For an oligomerization reaction, N is very generally less than 100. Oligomers are therefore generally defined as products of the oligomerization reaction that comprise less than 100 monomeric olefins. The preferred oligomerization reactions, however, involve the reactions where N is essentially less than 10, and in particular in which the major portion (by weight) of the oligomers is such that N is between 2 and 5 inclusive.

When N=2, 3 or 4, the associated oligomerization reactions are respectively named dimerization, trimerization or tetramerization reactions.

An oligomerization reaction rarely leads, in a selective way, to oligomeric olefins that all comprise an identical number N of monomeric olefins. The oligomerization reaction most often leads to a mixture of oligomeric olefins of a different number N, of which one can be in the majority.

The monomeric olefins that are suitable for the oligomerization reaction of the process of the invention most often comprise 2 to 20 carbon atoms per molecule and at least a double carbon-carbon bond. These monomeric olefins include, but are not limited to, acyclic monoolefins, cyclic monoolefins and diolefins.

In a preferred way, the monomeric olefins are acyclic monoolefins with 2 to 20 carbon atoms, pure or in a mixture. Non-limiting examples of these monomeric olefins are ethylene, propylene, butenes, pentenes, hexenes, octenes, nonenes, decenes, undecenes and dodecenes.

More preferably, the monomeric olefins are acyclic monoolefins of 2 to 10 carbon atoms, pure or in a mixture. Non-limiting examples of these monomeric olefins are: ethylene, propylene, butene-1, pentene-1, hexene-1, octene-1, and decene-1.

Even more preferably, the monomeric olefins are acyclic monoolefins with 2 to 6 carbon atoms, pure or in a mixture. Nonlimiting examples of these monomeric olefins are: ethylene, propylene, butene-1, butenes-2, isobutene, pentene-1, pentene-2, methyl-2-butene-1, methyl-2-butene-2, methyl-3-butene-1, hexene-1, hexene-2, hexene-3, methyl-2-pentene-1, methyl-3-pentene-1, methyl-4-pentene-1, methyl-2-pentene-2, methyl-3-pentene-2, methyl-4-pentene-2, dimethyl-2,3-butene-1, dimethyl-3,3-butene-1, and dimethyl-2,3-butene-2. Among these monoolefins, it is preferred to use ethylene, propylene or a mixture of the two.

The oligomerization of such monomeric olefins makes it possible to obtain products with high added value. The oligomerization of ethylene makes it possible, for example, to obtain terminal linear olefins such as butene-1, hexene-1, and octene-1 that are much used, for example, as co-monomers in the production of polyethylene. The oligomerization of propylene makes possible, for example, the synthesis of dimethylbutenes that are valued intermediate products in agrochemistry or perfume chemistry. The oligomerization of butenes in a mixture makes it possible, for example, to obtain octenes, intermediate products that are recognized for the synthesis of plasticizers of vinyl polychloride.

Stage a)

The process of the invention comprises a reaction stage a) for oligomerization of olefins. During this stage a), a monomeric olefin or a mixture of monomeric olefins is brought into contact with a catalyst for oligomerization to produce one or more oligomeric olefins.

The catalysts that make it possible to carry out the oligomerization reaction can be heterogeneous or homogeneous relative to the reaction medium. They generally comprise at least one of the following elements: a transition metal, an acid compound or a basic compound.

A nonlimiting example of a catalyst is the one of the industrial process that is known under the trade name Polynaphta©. This process is used for the oligomerization of butenes that are contained in a butenes/butanes mixture. It is a heterogeneous catalyst based on a Bronsted acid silica-alumina. This process is described in a Chimie Hebdo background article, No. 1294, p. 13, Apr. 11, 1997.

A second nonlimiting example of a catalyst is the catalyst that is known under the trade name Alfene©. It makes it possible to oligomerize the ethylene in a terminal linear olefin mixture. This catalyst is triethyl aluminum, Lewis acid, used in gaseous phase where the reaction takes place; it is therefore homogeneous with regard to the reaction medium. The process, the catalyst and the patents that relate thereto are described in the journal Catalysis Today (1992), 14, pp. 1-124.

The catalyst that is used for carrying out the oligomerization stage of the process of the invention preferably comprises a transition metal. This transition metal optionally can have a substrate.

A nonlimiting example of a catalyst is the industrial catalyst of the process Octol© for the oligomerization of butenes. It comprises a transition metal, nickel. The nickel has a substrate and is therefore heterogeneous with regard to the reaction medium. It is described in an article of Hydrocarbon Processing, Int. Ed. (1986), 65 2, Sect. 1, 31-33.

In the case where the catalyst does not have transition metal, the catalyst that is used in stage a) of the process of the invention is preferably a homogeneous catalyst with regard to the reaction medium and can comprise one or more transition metals of groups 4, 5, 6, 7, 8, 9, 10, 11 or 12 of the periodic table.

In the catalyst of stage a), the transition metal or each of the transition metals may or may not be associated with a ligand. The ligand is generally selected from the group that comprises hydrogen, halogens, alkyls, substituted alkyls, cycloalkyls, substituted cycloalkyls, heterocycloalkyls, substituted heterocycloalkyls, aryls, substituted aryls, heteroaryls, substituted heteroaryls, alkoxy, aryloxy, hydroxy, boryls, silyls, hydrido, thio, amines, phosphines, phosphonites, phosphinites, phosphites or one of their combinations.

The catalyst of stage a) is active for the oligomerization of olefins, optionally in combination with an activator. The activators that are known to one skilled in the art include in particular the aluminoxanes, the alkylmagnesiums, the halo-alkylmagnesiums, the alkoxymagnesiums, the aryloxymagnesiums, the strong Lewis acids such as the alkylaluminums, the halo-alkylaluminums, the alkoxyaluminums, the aryloxyaluminums, the alkylborons, the halo-alkylborons, the alkoxyborons, the aryloxyborons or one of their combinations.

One nonlimiting example of an oligomerization catalyst that comprises an activator is that of the Alphabutol© process of the Axens Company that is intended to oligomerize ethylene. The effluent of this process contains butene-1, dimerization product of ethylene, for the most part at more than 80% by weight. The catalyst that is used is based on titanium, transition metal, activated by a trialkylaluminum. The catalyst is soluble in the liquid phase where the reaction takes place; it is therefore homogeneous with regard to the reaction medium. This catalyst is described in the U.S. Pat. No. 4,532,370.

The reaction medium of stage a) can consist essentially of the feedstock, products and constituent elements of the catalyst, such as in the industrial oligomerization processes described above, or else it comprises in addition a diluent that is just added to the feedstock and in particular solubilizes the constituent elements of the catalyst.

A nonlimiting example of the reaction medium that comprises a diluent is that of the reaction stage of the process AlphaSelect© of which the catalyst comprises a transition metal, zirconium, a ligand of the acetal class, and a chloroalkyl aluminum activator of general formula $AlR_nX_{3-n}$ (where R is an alkyl group and X is a halogen such as chlorine or bromine, whereby n is the preferred number between 1 and 2). These constituent elements of the catalyst are used in the presence of a hydrocarbon diluent. The catalyst is soluble in this diluent, where the oligomerization reaction takes place; it is therefore homogeneous with regard to the reaction medium. This oligomerization process is described in the U.S. Pat. No. 5,345,023.

Reaction medium is defined as all of the phases (gaseous, liquid or solid) that are present in the reactor or reactors that are used to carry out the oligomerization reaction of stage a).

The oligomerization stage a) can be conducted in one or more reactor(s). The reactor or reactors can be any means known to one skilled in the art that is suitable to the use of the catalyst. For example, it is possible to use fixed-bed reactors, fluidized-bed reactors, circulating-bed reactors, catalytic columns or reactors that are suitable for the use of homogeneous catalysts.

The reaction medium can be stirred by a mechanical or magnetic stirring, by the introduction of a gas, a reagent or reagents, a catalyst or its constituent elements, a diluent, or by the recirculation of the reaction medium itself.

The reaction stage a) can be conducted in batch mode, semi-continuously or continuously. In a preferred way, the oligomerization reaction of stage a) is conducted in a continuous manner.

The temperature of the reaction during stage a) is suitable for the oligomerization of olefins. The reaction temperature of stage a) is preferably between 0 and 300° C., and more preferably between 10 and 210° C.

The pressure at which the oligomerization reaction medium is kept during stage a) is suitable for the oligomerization of olefins. The pressure of stage a) is preferably between atmospheric pressure (0.1 MPa) and 35 MPa, and preferably between 1 and 25 MPa.

The following examples of industrial processes are not limiting and illustrate the diversity of reaction conditions that can be used in the reaction stage of the oligoinerization process of the invention.

In the case of a Dimersol© process marketed by the Axens Company, propylene, butenes or their mixture are oligomerized in the presence of their homologous paraffins, without a diluent. Homologous paraffins are defined as the paraffins that have the same number of carbon atoms as the monomeric olefins that are being considered. The elements of the catalyst can comprise a transition metal, nickel, and an activator, a chloroalkyl aluminum of general formula $AlR_nX_{3-n}$, where R is an alkyl group and X is a halogen such as chlorine or bromine. The oligomerization reaction is operated in a series of reactors stirred by recirculation of the reaction medium and/or tubular reactors. A pressure, encompassed between 1 and 2 MPa, and a temperature, encompassed between 30 and 60° C., make it possible to keep the entire one-phase reaction medium in a single liquid phase. All of the constituent elements of the catalyst are soluble in this liquid reaction medium and are therefore homogeneous with regard to this reaction medium. This oligomerization process is described in the U.S. Pat. No. 5,345,023.

In the case of a SHOP© process (Shell Higher Olefins Process) marketed by the Shell Company, ethylene is oligomerized into a mixture of terminal linear olefins. A catalyst that comprises a transition metal, nickel, and a ligand of the phosphine class is generally used. The catalyst is soluble in a diluent, a butane diol; it is therefore homogeneous with regard to the reaction medium. The reaction is conducted between 80 and 120° C., at a pressure that is kept between 7 and 13 MPa. Under these conditions, the reaction medium is generally three-phase. The monomeric olefin, ethylene, is for the most part present in a gaseous phase. The diluent, in which the catalyst is solubilized, is not miscible with the liquid phase that is formed by the oligomeric olefins that are produced. The diluent and the oligomeric olefins form two liquid phases. All or part of the reaction medium is recirculated in each of the reactors so as to ensure the stirring of the reaction medium. The SHOP© process and the constituent elements of the catalyst are described in the journal Catalysis Today (1992), 14, 1-124.

The first effluent that is recovered during stage a) comprises oligomers, or more specifically oligomeric olefins, olefins or more specifically monomeric olefins that have not reacted, as well as inert compounds such as paraffins and optionally impurities.

The first effluent recovered during stage a) optionally can be passed into a stage for inhibiting the catalyst when the latter is homogeneous with regard to the reaction medium. This stage for neutralization of all catalytic activity makes it possible in particular to prevent the presence of the catalyst radicals from altering, by uncontrolled reaction, the purity of the products of the initial reaction.

The first effluent, optionally after a neutralization stage, is then sent into a separation stage b).

Stage b)

During the separation stage b), a portion of the oligomers contained in the effluent that comprises oligomers, paraffins and the monomeric olefins that have not reacted is separated.

Typically, the oligomeric olefins have a greater molecular weight than the monomeric olefins that have not reacted and than the paraffins that are associated with these monomeric olefins. In a general way, the monomeric olefins that have not reacted, the associated paraffins and the impurities have lower boiling points than the oligomers.

Thus, any means of separation known to one skilled in the art that take advantage of these fluctuations in volatility between the elements to be separated can be used. By way of examples, it is possible to use evaporators, series of evaporators, and, of course, distillation columns of any type. These means can also be combined in a series. The means of separation by adsorption, absorption or membrane separation can also be considered because of differences in polarities and sizes of molecules to be separated.

Stage b) of the process of the invention generally does not make it possible to separate all of the oligomers.

Separation stage b) preferably makes it possible to separate at least 50% by weight, preferably 60% by weight, and more preferably 80% by weight of the oligomers that are contained in the effluent that is obtained from stage a).

Stage c)

At the end of stage b), the mixture that comprises oligomers, paraffins and olefins is, at least in part, recycled into reaction stage a). In addition, this mixture can comprise impurities.

Stage d)

Membrane separation stage d) is used on another portion of the mixture that is obtained during separation stage b). This portion comprises oligomers, paraffins and the olefins that have not reacted during stage a).

This other portion of the mixture that is obtained during separation stage b) and that comprises oligomers, paraffins and olefins that have not reacted, corresponds, in fact, to a purging. In the prior art, this purging in general was not upgraded, or, sometimes, it was used as fuel in the factory.

This other portion of the mixture that is obtained during separation stage b) can represent between 1 and 99% by weight, preferably between 2 and 50% by weight, of said mixture.

During the membrane separation stage d), this portion of the mixture obtained during stage b) (or purging) is sent into membrane separation means. A permeate that comprises at least 70%, preferably at least 80%, and more preferably at least 90%, for example 96% by weight of olefins, and a retentate that comprises paraffins and oligomers, is drawn off.

Typically, the membranes that are used in the invention are permeable to monomeric olefins, preferably having 2 to 4 carbon atoms, according to the application being considered.

It was found that it was possible to use membranes, not only permeable to short olefins of 2 to 4 carbon atoms and fairly impermeable to associated paraffins having the same number of carbon atoms, but also having a reduced permeability to the formed oligomers. Without being linked to any theory, this discovery could be obtained from a very low diffusion rate of the oligomers relative to the short olefin extracted through the membrane. Actually, the increase in the number of carbon atoms in a molecule has a tendency to lead to a significant increase of the friction phenomena of said molecule within the rigid polymeric matrix of a membrane. In addition, whereby the oligomer is fairly unconcentrated in the feedstock relative to the short olefin, its flow density through the membrane has a tendency to be very low because of a very reduced transmembrane driving force.

Among the membrane materials that can be used during stage d) of the process of the invention, vitreous rigid polymers are preferred. The latter make it possible to effectively carry out the separation of short olefins from short paraffins. Vitreous polymer is defined in general as the polymers that have a vitreous transition temperature that is higher than ambient temperature and preferably higher than 100° C. With this type of material, the mass transfer is of the solution-diffusion type, and the separation is essentially due to a difference in rate of diffusion between the olefins, faster, and the paraffins, slower. This difference in diffusivity rests essentially in a kinetic diameter difference, the olefins being more "compact" than their paraffin homologs.

Among the preferred vitreous polymers for this olefin-paraffin separation, it is possible to cite, in a non-exhaustive manner, the following materials:

The PPO (phenyl polyoxide) and derivatives (Ilinitch, O. M., Semin, G. L., Chertova, M. V., Zamaraev, K. I., Novel Polymeric Membranes for Separation of Hydrocarbons, J. Membr. Sci. 66 (1992) 1-8), particularly effective for the ethylene/ethane separation, The polyimides and the polymer alloys using polymides, the polymides based on 6FDA-type dianhydride (4,4'-(hexafluoroisopropylidene)diphthaleic acid) including 6FDA-TrMP (polyimide obtained from the condensation of a 6FDA-type dianhydride and a trimethylphenylene amine-type diamine) and 6FDA-TeMP (polyimide obtained from the condensation of a 6FDA-type dianhydric acid and a tetramethylphenylene amine-type diamine) that have an advantageous permeability/selectivity pair for the propylene/propane separation (SHIMAZU, A., Miyazaki, T., Maeda, M., Ikeda, K., Relationship Between the Chemical Structures and the Solubility, Diffusivity and Perinselectivity of Propylene and Propane in 6FDA-Based Polyimides, J. Polym. Sci. (B) 38 (2000) 2525-2536; Tanaka, K., Taguchi, A., Hao, J., Kita, H., Okamoto, K., Permeation and Separation Properties of Polyimide Membranes to Olefins and Paraffins, J. Membr. Sci. 121 (1996) 197), Polyamides, Aromatic polyamides, Polyether imides, Polyvinyl pyrrolidones, Polycarbonates, and Mixtures of polymers or copolymers using at least one of the cited polymers.

The materials cited above can be used in plane, spirally wound or tubular form, or preferably in the form of hollow fibers, geometries that offer the best performance levels in terms of compactness.

The membranes that use the materials cited above preferably are used in "gas permeation/vapor" mode. In this configuration, the mixture that is introduced in stage d) returns in vapor phase upstream from the membrane at a total pressure of more than that of the compartment that is downstream from the membrane in which the short olefin-enriched permeate is collected. The temperature that is being considered for this type of separation is generally between −20° C. and 200° C., preferably between ambient temperature and 150° C., and preferably between 30° C. and 100° C.

Other types of use of the membranes cited above can be considered, in particular for mixtures introduced at this stage d) in liquid form. Examples of technologies are the pervaporation that combines the permeation through a dense membrane with the vaporization of the permeate downstream from the membrane, and hyperfiltration, for which the permeate is recovered in liquid phase. The economic advantage of these membrane separation modes is sometimes less pronounced than in the case of the gas/vapor permeation because these technologies typically require the use of a compressor to liquefy the purging.

Among the membrane materials that can be used during this stage d) of the process of the invention, it is possible to use membrane materials that use selectivity mechanisms based on affinity phenomena. This type of material, however, is often less easy to use or more costly. Among these materials, it is possible to cite in a non-exhaustive manner the polymers that are impregnated with metal salts, such as the silver salts (Muller, J.; Peinemann, K. V.; Muller, J. Development of Facilitated Transport Membranes for the Separation of Olefins from Gas Streams, Desalination, 145 (1-3): 339-345, 2002) (development of membranes with improved passage for the separation of olefins in gas streams).

In a preferred embodiment, the retentate is sent into a stage e) for separation, typically by condensation, making it possible to separate the oligomers from the paraffins.

In this embodiment, the purpose is to upgrade the oligomeric olefins that are normally purged with the paraffins, at best with an energy upgrade, otherwise without any upgrading. This separation of stage e) can be done by any type of separation that is known to one skilled in the art, such as, for example, by condensation, evaporation, distillation, adsorption, absorption or membrane separation. At the end of this separation stage e), a paraffin stream that is low in oligomeric olefins and a stream that is high in oligomeric olefins that, according to its degrees of purity, can be sent directly to the storage of finished or recycled product in the process, are recovered.

The primary advantage of this embodiment is to increase the overall output of the process by recovering a portion of the oligomeric olefins of high added value, which are concentrated in the retentate.

Separation stage e) that makes it possible to separate the oligomers from the paraffins is preferably carried out by condensation.

The implementation by condensation of separation stage e) makes it possible to take advantage of the case where the olefins and the paraffins are in gaseous form. The oligomeric olefins having a higher condensation temperature than the paraffins; the condensation actually is present as a preferred separation means. This mode is particularly advantageous in the case where stage d) is carried out by gas/vapor permeation and less suitable in the case where this same stage d) is carried out by pervaporation.

In the case where separation stage e) is carried out by condensation, the retentate in vapor form that is obtained from stage d) is cooled to a temperature that makes it possible to condense it at least partially. Then, by a liquid/vapor separation, for example in a flash tank (separator tank), in general a liquid stream that is high in oligomeric olefins is obtained, whereby the latter can be upgraded or sent to the storage of the finished product. In parallel, a vapor stream that essentially comprises paraffins and that can be sent to a purging circuit is obtained.

The condensation that is used in stage e) is facilitated by membrane separation stage d), which imparts a synergy effect between these two stages. It appears that the membrane separation stage d) makes it possible to concentrate the oligomers in the retentate, which makes it possible to carry out the condensation of stage e) at a higher heat level, which requires a slighter cooling. As a result, the separation by condensation of stage e) is conducted economically. Increased recovery can also be obtained, in particular at an identical condensation temperature. Moreover, this condensation of stage e) combined with the membrane separation of stage d) makes it possible to obtain a high-purity oligomeric olefin liquid stream.

The permeate is typically recycled in the reaction stage.

This embodiment can be carried out with a supply compressor for bringing the pressure of the gaseous permeate of stage d) to a level that is compatible with the reaction zone a). This embodiment makes it possible to increase the overall yield of the process because the monomeric olefins are converted into oligomeric olefins.

DETAILED DESCRIPTION OF THE FIGURES

Figure 2:
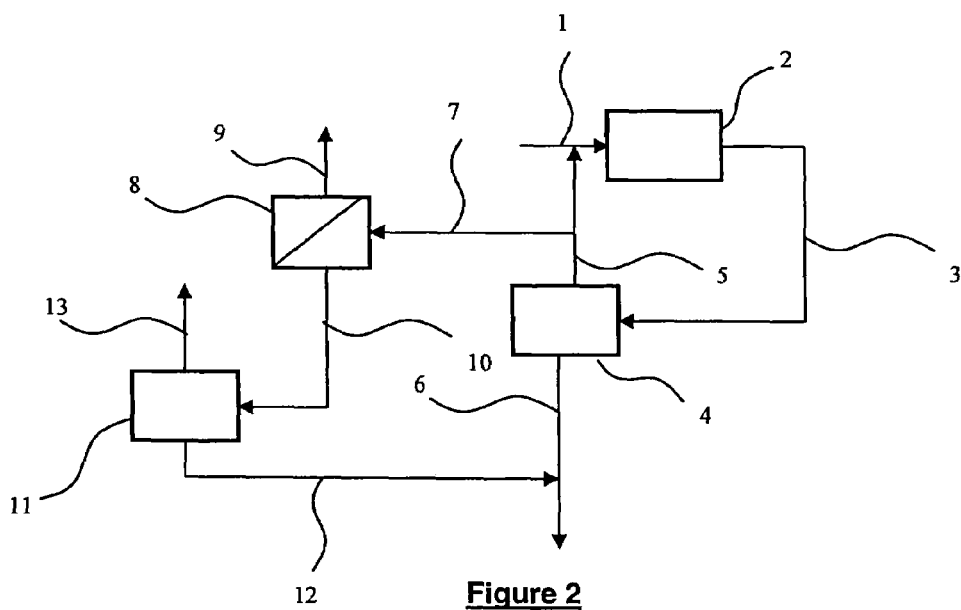
FIG. 2 illustrates, in a nonlimiting manner, an embodiment in which the retentate is sent into a separation stage that makes it possible to separate the oligomers from the paraffins.
Figure 3:
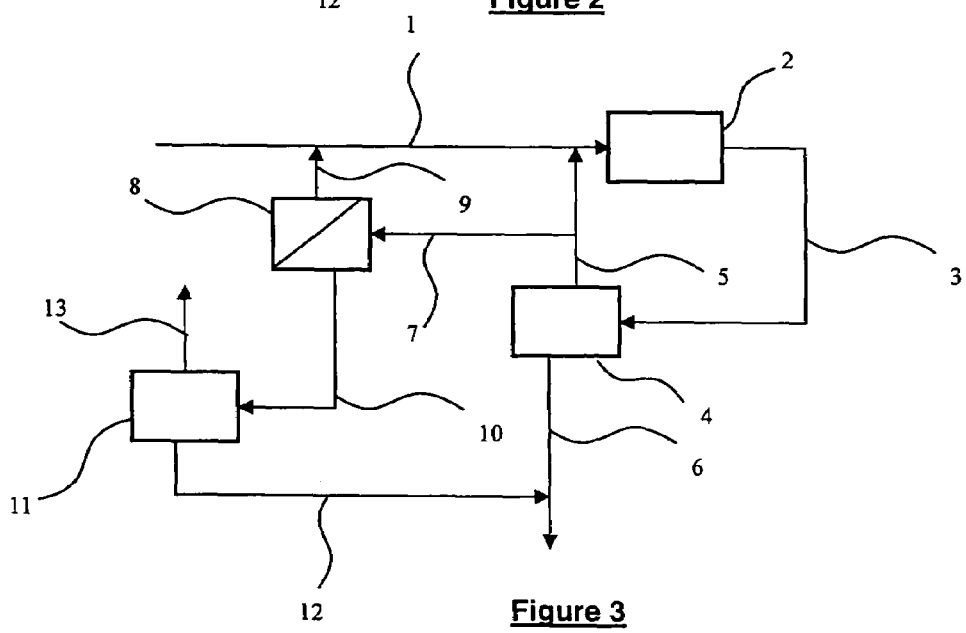
FIG. 3 illustrates, in a nonlimiting manner, an embodiment that includes the elements of FIG. 2, in which the permeate is recycled in the reaction stage.

For a better understanding, several embodiments of the process of the invention are illustrated by FIGS. 1 to 3. These embodiments are provided by way of examples and do not have any limiting nature. These illustrations of the process of the invention do not comprise all of the components that are necessary for its implementation. Only the elements that are necessary for the understanding of the invention are shown there, whereby one skilled in the art is able to complete these representations to carry out and implement the invention.

FIG. 1 shows the principal stages of the process of the invention. The supply of the monomeric olefin feedstock is carried out via a pipe 1 to an oligomerization reactor 2. The oligomerization product is evacuated from the reactor 2 via a pipe 3 to be sent into a separation stage 4 into which a portion of the product of the reaction is separated from light olefins that have not reacted. This separation stage is generally one or more successive flashes (separator tanks with liquid-vapor equilibrium) or else a distillation column. The light olefins that have not reacted are then recycled at the inlet of the reactor 2 via a recycling pipe 5, whereas the oligomer that is obtained is evacuated via a pipe 6. A sample of a stream of purged material is taken from the recycling pipe 5 via a purging pipe 7. The latter makes it possible to continuously evacuate a portion of the short paraffins that enter the reactor 2, which otherwise would accumulate in a loop formed by the referenced elements 1, 2, 3, 4 and 5.

The purging stream is sent via the purging pipe 7 to a separation stage 8 that uses a membrane that is selective only for monomeric olefins. These short olefins, i.e., the permeate, are recovered via a pipe 9. The membrane of the membrane separation stage 8 is fairly impermeable to oligomers and to the short paraffins that are present in the purging stream. Thus, the oligomers and the short paraffins, constituting the retentate, are separated and recovered in a pipe 10.

FIG. 2 shows an embodiment, including the elements of FIG. 1, in which the retentate, via the pipe 10, is sent into a separation stage 11 that makes it possible to separate the oligomers from the paraffins. The oligomers that have a high added value are recycled, via a pipe 12, into the pipe 6 for evacuating oligomers that are exiting from the reactor 2 or are downstream from the latter. The paraffins are recovered via the pipe 13. This mode makes it possible to improve the overall oligomer output.

FIG. 3 shows an embodiment, including the elements of FIG. 2, in which the permeate that is recovered via the pipe 9 is recycled to the reaction stage.

In reference to the figures, and in particular to FIG. 3, in general flows of material as indicated are used as follows:

At the outlet of the first separation stage b) (referenced 4), the amount of oligomers recycled to the reactor 2 via the terminal portion of the pipe 5 in general represents between 2% and 35%, often between 3% and 25%, and most often between 5% and 15% by weight of the total amount of oligomers entering the separation (referenced 4) via the pipe 3.

The level of oligomers contained in the purging that supplies the membrane separation of stage d) (via the pipe 7) is generally between 1% and 25%, in particular between 1.5% and 15%, often between 2% and 10% by weight of the total amount of oligomers of the separated overall mixture that is obtained in stage b) (circulating in the initial portion of the pipe 5).

The concentration of oligomers in the purging (pipes 5 and 7) is in general encompassed between 1 mol % and 50 mol %, often between 2 mol % and 30 mol %, and more particularly between 4 mol % and 20 mol %.

The molar concentration of oligomers of the retentate (pipe 10) is generally between 1.2 and 6× greater and often between 1.5 and 3× greater than that at the input of the membrane separation of stage d) (pipe 7).

The second separation stage e) makes it possible to recover between 15% and 95%, in particular between 20% and 90%, and most often between 30% and 70% by weight of the oligomers of the purging (supplying the membrane separation via the pipe 7).

The use of a membrane separation is perfectly suitable for the process of the invention in the three embodiments described above, for the following reasons:

- It is designed to treat low flows (on the order of 100 kg/h for a unit of 20,000 t/year of butene-1), hence a small useful membrane surface area
- The membrane materials that are used are not expensive (polymer)
- Because of the small membrane surface area to be used and the compactness of this type of module, the addition of an operation for recovery of olefins of the type described in the invention in existing oligomerization units is very easy
- The process is financially efficient and allows a very quick return on investment.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding International Application No. PCT/FR06/00535, filed Mar. 10, 2006, and French Application Serial No. 05/03.600, filed Apr. 11, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLE

The example presented below makes it possible to illustrate the advantages of the process of the invention. This example essentially consists of a digital simulation. The process that is illustrated by this example is dedicated to the recovery of the ethylene and butene-1 in a purging gas from a process for the production of butene-1 by oligomerization of ethylene.

The embodiment that is shown in FIG. 3 was used as a basis for this example.

The reaction stage a) uses, in a reactor 2, a catalyst that is based on titanium, transition metal, activated by a trialkyl aluminum. The reactor 2 is supplied with polymer-grade feedstock ethylene via the pipe 1. The effluent in the pipe 3 comprises butene-1, produced from the dimerization of ethylene, with a content of 80% by weight, whereby the remainder consists essentially of ethylene that has not reacted, paraffins and traces of inert substances that are introduced with the ethylene of the feedstock or obtained from undesired reactions.

The effluent of the pipe 3 that is obtained from the reactor 2 is then sent to a distillation column 4. This column is designed to separate 90% by weight of butene-1, present in the effluent that is obtained from the reactor, from a mixture that contains unconverted ethylene, paraffins and inert substances, as well as an amount of butene-1 that corresponds to 10% by weight of the amount that is present in the effluent of the reactor. The mixture that is thus recovered at the top of the column is recycled to the reaction stage a) via the pipe 5.

A sample of purged material is taken from the pipe 5 into the pipe 7 so as to deconcentrate the paraffins and impurities. It should be noted that in the standard processes, this purging is generally sent to the torch network with a zero upgrading or, at best, is used as a fuel, with an energy upgrade that is equivalent to that of natural gas.

In the process of this example according to the invention, the purging stream of the pipe 7 is sent to a membrane separation stage d) that operates in gas/vapor permeation so as to draw off, on the one hand, a permeate into the pipe 9 that comprises 87% by weight of the ethylene that is contained initially in the purging (pipe 7), with a purity of 96% by weight, and, on the other hand, a retentate into the pipe 10 that comprises the paraffins and impurities, the butene-1 and the ethylene remaining. The permeate of the pipe 9 is recycled to the reactor 2.

The membrane that is used for this example has a selective layer of a 1 μm thickness that consists of phenylene polyoxide. The operating conditions within the membrane module are as follows: temperature =50° C., pressure upstream from the membrane (retentate compartment)=2.5 MPa, pressure downstream from the membrane ("permeate" compartment)= 1 MPa.

The retentate of the pipe 10 is sent to a condensation stage e). During this condensation stage e), a liquid phase that comprises the condensed butene-1 is cooled and is flash-separated in a pipe 12 from a vapor phase that comprises the paraffins and impurities in a pipe 13. The vapor phase of the pipe 13 is sent to the torch network with a zero upgrade or, at best, to be used as a fuel with an energy upgrade that is equivalent to that of natural gas. The liquid phase of the pipe 12 is mixed with the mixture that circulates in the pipe 6.

The following tables provide the compositions and the total flow rates of the streams at different points of the installation according to FIG. 3.

|  | Pipe 5: Flow of Recycled Material to the Reactor | Pipe 7: Flow of Purged Material | Pipe 9: Permeate Recycled to the Reactor |
|---|---|---|---|
| Paraffins, Impurities (% by Weight) | 4.40 | 4.40 | 4.00 |
| Ethylene (% by Weight) | 65.60 | 65.60 | 96.00 |
| Butene-1 (% by Weight) | 30.00 | 30.00 | 0.00 |
| Total (% by Weight) | 100.00 | 100.00 | 100.00 |
| Total Flow Rate (kg/h) | 1000 | 35 kg/h | 20.8 |
| Temperature (° C.) | 50 | 50 | 50 |
| Pressure (MPa) | 3.0 | 3.0 | 1.0 |

-continued

|  | Pipe 10: Retentate to Condensation | Pipe 12: Condensed Butene-1 | Pipe 13: Purged Vapor Phase |
|---|---|---|---|
| Paraffins, Impurities (% by Weight) | 4.90 | 1.60 | 7.80 |
| Ethylene (% by Weight) | 21.10 | 5.20 | 34.90 |
| Butene-1 (% by Weight) | 73.90 | 93.20 | 57.30 |
| Total (% by Weight) | 100.00 | 100.00 | 100.00 |
| Total Flow Rate (kg/h) | 14.2 | 6.6 | 7.6 |
| Temperature (° C.) | 50 | 35 | 35 |
| Pressure (MPa) | 2.5 | 1.0 | 1.0 |

The process of the invention makes it possible to limit the losses of hydrocarbons to the torch network or the use, with a slight upgrade, as fuel. Actually, only 7.6 kg/h of hydrocarbons is thus not upgraded or is slightly upgraded, relative to a total purging of 35 kg/h on the mixture that is recycled in the pipe 5. The difference is upgraded as raw material for the ethylene stream from the pipe 9 that is recycled to the reaction stage and recycled downstream from the reaction section as a product (oligomer, in this case dimer) for the stream of the pipe 12. This has an impact on the overall yield of the process by reducing the losses of hydrocarbons and by maximizing the recycling of the reagents of high added value and the recovery of the desired product.

The ivention claimed is:

1. Process for the oligomerization of olefins that have 2 to 6 carbon atoms, comprising at least:
  a) One reaction stage in which a first effluent that comprises oligomers, paraffins and olefins that have not reacted is recovered,
  b) At least one separation stage that makes it possible to separate a portion of the oligomers that are contained in the effluent from a mixture that comprises oligomers, paraffins and the olefins that have not reacted,
  c) Recycling of a portion of said mixture in the reaction stage, and
  d) A stage for membrane separation of another portion of said mixture so as to draw off a permeate that comprises at least 70% by weight of olefins and a retentate that comprises paraffins and oligomers,
  e) At least one stage for separation of at least one portion of the oligomers from said retentate.

2. Process according to claim 1, in which between 15% and 95% by weight of the oligomers contained in the supply of the membrane separation stage are recovered in stage e).

3. Process according to claim 2, in which the olefins are acyclic monoolefins with 2 to 6 carbon atoms, pure or in a mixture.

4. Process according to claim 3, in which the olefins are essentially ethylene.

5. Process according to claim 3, in which the olefines are essentially propylene.

6. Process according to claim 3, in which the olefins are essentially a mixture of ethylene and propylene.

7. Process according to claim 1, in which the catalyst that is used for carrying out the reaction stage a) comprises a transition metal.

8. Process according to claim 1, in which the catalyst that is used in stage a) is a catalyst that is homogeneous with regard to the reaction medium and comprises one or more transition metals of groups 4, 5, 6, 7, 8, 9, 10, 11 or 12 of the periodic table.

9. Process according to claim 1, in which the reaction temperature of stage a) is between 0 and 300° C.

10. Process according to claim 1, in which the pressure of stage a) is between the atmospheric pressure (0.1 MPa) and 35 MPa.

11. Process according to claim 1, in which the membranes that are used are vitreous rigid polymers.

12. Process according to claim 1, in which the membranes are used in "gas/vapor permeation" mode.

13. Process according to claim 1, in which the separation stage e) that makes it possible to separate the oligomers from the paraffins is carried out by condensation.

14. Process according to claim 1, in which the permeate is recycled in the reaction stage.

* * * * *